US010799691B2

(12) United States Patent
Uemura et al.

(10) Patent No.: US 10,799,691 B2
(45) Date of Patent: Oct. 13, 2020

(54) NEEDLE ASSEMBLY FOR TRANSDERMAL ADMINISTRATION AND METHOD OF PRODUCING THE SAME

(71) Applicant: TOPPAN PRINTING CO., LTD., Taito-ku (JP)

(72) Inventors: Daizo Uemura, Taito-ku (JP); Kazuhiko Shiomitsu, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 133 days.

(21) Appl. No.: 15/586,447

(22) Filed: May 4, 2017

(65) Prior Publication Data

US 2017/0232246 A1    Aug. 17, 2017

Related U.S. Application Data

(63) Continuation of application No. PCT/JP2015/080587, filed on Oct. 29, 2015.

(30) Foreign Application Priority Data

Nov. 7, 2014  (JP) ................................ 2014-226794

(51) Int. Cl.
*A61M 37/00* (2006.01)
*B29C 43/02* (2006.01)
(Continued)

(52) U.S. Cl.
CPC ....... *A61M 37/0015* (2013.01); *B29C 43/021* (2013.01); *A61M 2037/0023* (2013.01);
(Continued)

(58) Field of Classification Search
CPC ........... A61M 37/0015; B29C 33/3857; B29C 43/021
See application file for complete search history.

(56) References Cited

U.S. PATENT DOCUMENTS 6,183,434 B1 * 2/2001 Eppstein ............ A61B 5/14514
424/449
7,347,835 B2    3/2008 Maenosono et al.
(Continued)

FOREIGN PATENT DOCUMENTS

JP    2000-513971 A    10/2000
JP    2001-309977 A    11/2001
(Continued)

OTHER PUBLICATIONS

International Search Report dated Jan. 19, 2016 in PCT/JP2015/080587, filed Oct. 29, 2015.
(Continued)

*Primary Examiner* — Jenna Zhang
(74) *Attorney, Agent, or Firm* — Oblon, McClelland, Maier & Neustadt, L.L.P.

(57) ABSTRACT

A needle assembly for transdermal administration including a substrate having a first surface and a second surface opposite to the first surface, and fine needles projecting perpendicularly from the first surface. The substrate has grooves on at least one of the first surface and the second surface, and the grooves are formed such that the substrate is deformable following a surface shape of a skin to allow axes of the fine needles to extend in a direction normal to the surface of the skin.

20 Claims, 8 Drawing Sheets

(51) Int. Cl.
  *B29C 33/38* (2006.01)
  *B29L 31/00* (2006.01)
(52) U.S. Cl.
  CPC .. *A61M 2037/0053* (2013.01); *B29C 33/3857* (2013.01); *B29C 2043/022* (2013.01); *B29L 2031/756* (2013.01); *B29L 2031/7544* (2013.01)

(56) References Cited

U.S. PATENT DOCUMENTS

| | | | |
|---|---|---|---|
| 9,089,677 B2* | 7/2015 | Soo | A61M 37/0015 |
| 2002/0010412 A1* | 1/2002 | Eppstein | A61M 37/0092 604/10 |
| 2002/0045907 A1 | 4/2002 | Sherman et al. | |
| 2002/0082543 A1* | 6/2002 | Park | A61N 1/30 604/21 |
| 2002/0133129 A1 | 9/2002 | Arias et al. | |
| 2004/0146611 A1 | 7/2004 | Arias et al. | |
| 2006/0127465 A1 | 6/2006 | Maenosono et al. | |
| 2010/0274203 A1 | 10/2010 | Lee et al. | |
| 2012/0220981 A1* | 8/2012 | Soo | A61M 37/0015 604/506 |

FOREIGN PATENT DOCUMENTS

| | | |
|---|---|---|
| JP | 2004-516868 A | 6/2004 |
| JP | 2005-021677 A | 1/2005 |
| JP | 2008-29710 A | 2/2008 |
| JP | 2009-82206 A | 4/2009 |
| JP | 2009-240410 A | 10/2009 |
| KR | 10-2011-0092914 A | 8/2011 |
| KR | 20110092914 A * | 8/2011 ........ A61M 37/0015 |
| WO | WO 02/072189 A2 | 9/2002 |
| WO | WO-2012103257 A3 * | 1/2013 ........ A61M 37/0015 |

OTHER PUBLICATIONS

Supplementary European Search Report dated Jun. 15, 2018 in European Patent Application No. 15856973.1, citing documents AA, AO and AP therein, 24 pages.

* cited by examiner

NEEDLE ASSEMBLY FOR TRANSDERMAL ADMINISTRATION AND METHOD OF PRODUCING THE SAME

CROSS-REFERENCE TO RELATED APPLICATIONS

The present application is a continuation of International Application No. PCT/JP2015/080587, filed Oct. 29, 2015, which is based upon and claims the benefits of priority to Japanese Application No. 2014-226794, filed Nov. 7, 2014. The entire contents of these applications are incorporated herein by reference.

BACKGROUND OF THE INVENTION

Field of the Invention

The present invention relates to a needle assembly for transdermal administration and a method of producing the same. In particular, the invention relates to a needle assembly for transdermal administration, in which a plurality of fine needles are integrally formed in the front surface of a substrate, and a method of producing the same.

Discussion of the Background

Percutaneous absorption is a method of delivering medicines into the body by osmosis through the skin. Percutaneous absorption is used as a convenient method for painless medication administration; however, percutaneous absorption is difficult for some types of medicines. Recent attention has focused on a method of allowing the body to absorb such medicines efficiently. This method involves piercing the skin with a micron-size fine needle body (i.e., a microneedle) and directly administering medicines into the skin. This method eliminates the need for using conventional syringes, thus simplifying the administration of medicines into the skin (see PTL 1). Such a fine needle body is required to have a thinness and a tip angle sufficient to pierce the skin, and a length sufficient for subcutaneous delivery of a liquid medicine. The needle body preferably has a conical shape whose diameter ranges from several micrometers to some hundreds of micrometers, and whose length ranges from some tens of micrometers to some hundreds of micrometers for the needle body to penetrate the horny layer, which is the outermost layer of the skin, but not to reach nerve cells.

Specifically, the needle body is required to penetrate the horny layer, which is the outermost skin layer having a thickness of about 20 µm, although the thickness of the horny layer depends on parts of the skin. Beneath the horny layer is the epidermis having a thickness ranging from about 200 µm to 350 µm, and beneath the epidermis is the dermis housing an extensive network of capillaries. This structure requires a needle to have a length of at least 20 µm to penetrate the horny layer so that a liquid medicine is permeated. In producing a needle body for blood sampling, the needle body is required to be designed with a length of at least 350 µm, considering the above-described skin structure.

The material for the needle body needs to be harmless to the human body even if a broken piece of the needle body remains in the human body. As such materials, biocompatible resins such as a medical silicone resin, maltose, polylactic acid, and dextran are considered to be suitable (see PTL 2).

Some mechanisms for administering medicines into the body have been proposed. In one mechanism, a medicine is applied to the surface of a needle and the skin is pierced with this needle to thereby administer the medicine. In another mechanism, a hollow needle or a needle body having fine holes for passage of a liquid medicine is used to administer a liquid medicine from a substrate surface attached to the body (see PTL 3).

A method of improving the performance of a needle body in the administration of medicines is described in PTL 4. According to this method, grooves are formed in a side surface of the needle portion to assist delivery of compounds.

PTL 1: U.S. Pat. No. 6,183,434 B1
PTL 2: JP-A-2005-021677
PTL 3: JP-A-2001-309977
PTL 4: JP-A-2004-516868

SUMMARY OF THE INVENTION

According to an aspect of the present invention, a needle assembly for transdermal administration including a substrate having a first surface and a second surface opposite to the first surface, and fine needles projecting perpendicularly from the first surface. The substrate has grooves on at least one of the first surface and the second surface, and the grooves are formed such that the substrate is deformable following a surface shape of a skin to allow axes of the fine needles to extend in a direction normal to the surface of the skin.

According to another aspect of the present invention, a method of producing a needle assembly for transdermal administration, includes producing an original plate which includes a substrate-forming part and has, on a surface of the substrate-forming part, a needle-forming part and a groove-forming part, forming a reproduction plate based on the original plate such that the reproduction plate includes a flat part corresponding to the substrate-forming part, a recess corresponding to the needle-forming part, and a linear projection corresponding to the groove, placing a polymer material on a surface of the reproduction plate having the flat part, the recess, and the linear projection, heating the polymer material such that the polymer material is melted, pressing melted polymer material by a press including a flat surface portion facing the flat part and a projecting portion formed in the flat surface portion which extends in a direction parallel to or perpendicular to a direction in which the groove-forming part extends, curing the polymer material such that a needle assembly is formed, and releasing the needle assembly from the reproduction plate to obtain the needle assembly including fine needles and a substrate having a groove formed such that the substrate is deformable following a surface shape of a skin.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2(a) illustrates a first exemplary arrangement of grooves formed in the front surface of the needle assembly, and FIG. 2(b) illustrates a first exemplary arrangement of grooves formed in the rear surface of the needle assembly.

FIG. 9(a) illustrates a second exemplary arrangement of the grooves formed in the front surface of the needle assembly, and FIG. 9(b) illustrates a second exemplary arrangement of the grooves formed in the rear surface of the needle assembly.

FIG. 10(a) illustrates a third exemplary arrangement of the grooves formed in the front surface of the needle assembly, and FIG. 10(b) illustrates a third exemplary arrangement of the grooves formed in the rear surface of the needle assembly.

FIG. 11(a) illustrates a fourth exemplary arrangement of the grooves formed in the front surface of the needle assembly, and FIG. 11(b) illustrates a fourth exemplary arrangement of the grooves formed in the rear surface of the needle assembly.

FIG. 12(a) illustrates a fifth exemplary arrangement of the grooves formed in the front surface of the needle assembly, and FIG. 12(b) illustrates a fifth exemplary arrangement of the grooves formed in the rear surface of the needle assembly.

FIG. 13(a) illustrates a sixth exemplary arrangement of the grooves formed in the front surface of the needle assembly, and FIG. 13(b) illustrates a sixth exemplary arrangement of the grooves formed in the rear surface of the needle assembly.

DESCRIPTION OF THE EMBODIMENTS

Figure 1:
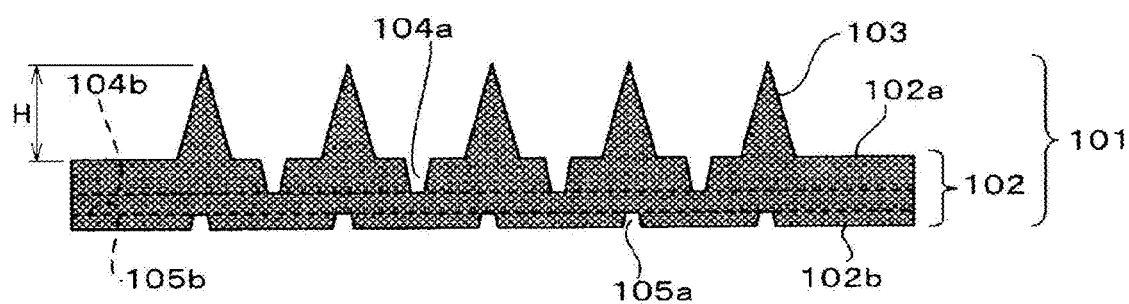
FIG. 1 is a longitudinal sectional view of a needle assembly for transdermal administration, according to an embodiment of the present invention.

The embodiments will now be described with reference to the accompanying drawings, wherein like reference numerals designate corresponding or identical elements throughout the various drawings.

Embodiment

Figure 2A:
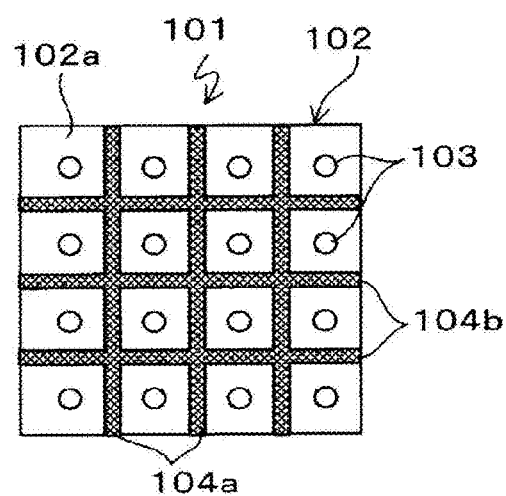
FIGS. 2(a) and 2(b) are plan views of the needle assembly illustrated in FIG. 1.
Figure 2B:
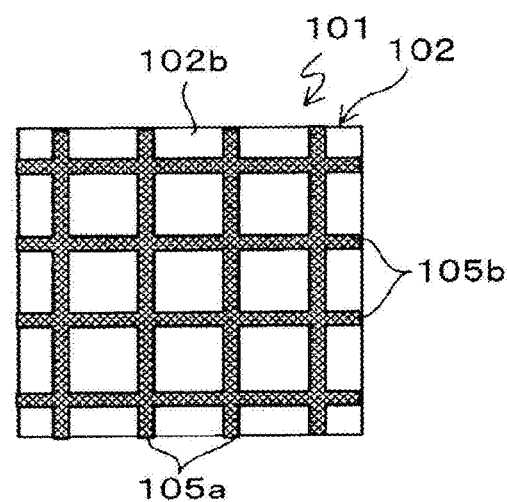

With reference to FIGS. 1-2(b), an embodiment of a needle assembly for transdermal administration 101 will now be described.

As illustrated in FIG. 1, the needle assembly 101 of the present embodiment includes a substrate 102. One surface of the substrate 102 in a thickness direction is a front surface 102a, and the other surface of the substrate 102 in the thickness direction is a rear surface 102b. The front surface 102a is an example of the first surface, and the rear surface 102b is an example of the second surface. The needle assembly 101 includes a plurality of fine needles 103 projecting perpendicularly from the front surface 102a and arranged in a matrix at regular intervals along longitudinal and lateral directions of the front surface 102a.

The fine needles 103 of the needle assembly 101 according to the present embodiment have a height H which preferably ranges from 50 µm to 2000 µm, inclusive. More preferably, the height H of the fine needles 103 in the needle assembly 101 according to the present embodiment preferably ranges from 50 µm to 1000 µm, inclusive. The height H of each fine needle 103 is defined as a distance from the front surface 102a of the substrate 102 to the tip of the fine needle 103.

As illustrated in FIG. 2 (a), a group of fine needles 103 disposed in the longitudinal direction of the front surface 102a is defined as one column, and a group of fine needles 103 disposed in the lateral direction of the front surface 102a is defined as one row. The front surface 102a of the substrate 102 includes a plurality of first linear grooves 104a each formed along the column direction of fine needles 103 and located between adjacent columns of fine needles 103 so as to extend along the entire length of the substrate 102 in the longitudinal direction. That is, the first grooves 104a each extend in the longitudinal direction, which is an example of the first direction, and are arranged in the lateral direction, which is an example of the second direction perpendicular to the longitudinal direction.

The front surface 102a of the substrate 102 further includes a plurality of second grooves 104b each formed along the row direction of fine needles 103 and located between adjacent rows of fine needles 103 so as to extend along the entire length of the substrate 102 in the lateral direction and thus to cross the first grooves 104a. That is, the second grooves 104b extend in the lateral direction, which is an example of the first direction, and are arranged in the longitudinal direction, which is an example of the second direction that intersects the lateral direction.

As illustrated in FIG. 2 (b), the rear surface 102b of the substrate 102 includes a plurality of linear third grooves 105a each formed along the column direction of fine needles 103 so as to extend along the entire length of the rear surface 102b in the longitudinal direction. That is, the third grooves 105a extend in the longitudinal direction, which is an example of the third direction, and are arranged in the lateral direction, which is an example of the fourth direction perpendicular to the longitudinal direction.

The rear surface 102b of the substrate 102 includes a plurality of linear fourth grooves 105b each formed along the row direction of fine needles 103 so as to extend along the entire length of the substrate 102 in the lateral direction and thus to cross the third grooves 105a. That is, the fourth grooves 105b extend in the lateral direction, which is an example of the fourth direction, and are arranged in the longitudinal direction, which is an example of the fourth direction that intersects the lateral direction.

The positions of the grooves 105a and 105b in the rear surface 102b are offset from those of the grooves 104a and 104b in the front surface 102a as seen perpendicular to the front surface 102a.

In the above-configured needle assembly 101, the front surface 102a of the substrate 102 has fine needles 103 each positioned in a surface portion surrounded by the first and second grooves 104a and 104b extending, respectively, along the column direction and row direction. In the rear surface 102b of the substrate 102, the third grooves 105a extending along the column direction intersect the fourth grooves 105b extending along the row direction. The fine needles 103 in the front surface 102a are located at positions corresponding to the respective intersections of the third and fourth grooves 105a and 105b in the rear surface 102b.

The first, second, third, and fourth grooves 104a, 104b, 105a, and 105b each have a trapezoidal cross section perpendicular to the directions in which the grooves extend. The cross-sectional shape of the first grooves 104 and the second grooves 105 is not limited to the trapezoidal shape illustrated in FIG. 14 (a), but may be rectangular, triangular, semicircular, semielliptical as illustrated in FIGS. 14 (b) to 14 (d), respectively, or any combination thereof. That is, the plurality of grooves in each surface of the substrate 102 may include at least one type of grooves selected from among rectangular cross section grooves, triangular cross section grooves, semicircular cross section grooves, and semielliptical cross section grooves.

The grooves may have any dimensions, but their width W preferably ranges from 50 μm to 1000 μm, inclusive, and more preferably, from 100 μm to 300 μm, inclusive. The grooves have a depth D which preferably ranges from 50 μm to 1000 μm, inclusive, and more preferably, from 100 μm to 300 μm, inclusive.

The first grooves 104 are constituted by the first grooves 104a and the second grooves 104b, while the second grooves 105 are constituted by the third grooves 105a and the fourth grooves 105b.

Figure 3:
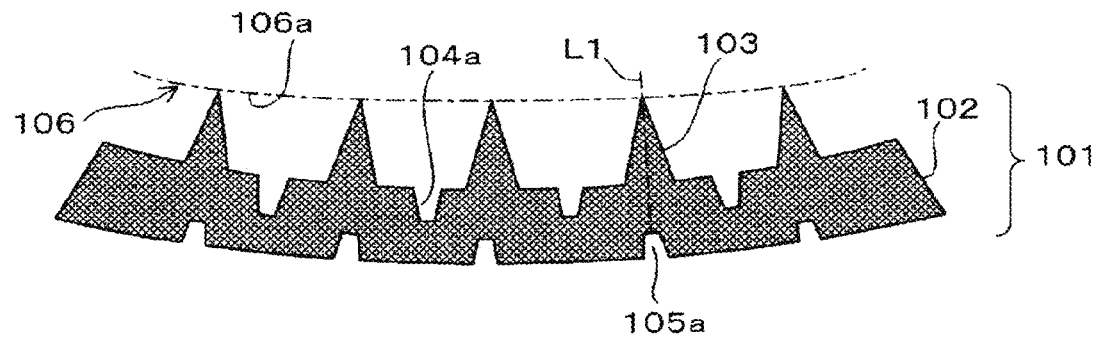
FIG. 3 is an exemplary cross-sectional view of the needle assembly illustrated in FIG. 1, with the needle assembly bent following a surface of the skin of the body.

In the above-configured needle assembly 101, the first and second grooves 104a and 104b are formed in the front surface 102a of the substrate 102, and the third and fourth grooves 105a and 105b are formed in the rear surface 102b of the substrate 102. This structure allows the needle assembly 101 to bend following a curved surface shape assumed by a skin 106a of a body 106, as illustrated in FIG. 3. This, in turn, allows a vertical axis L1 of each of the fine needles 103 to be displaced in a direction coinciding with the line normal to the curved surface of the skin 106a of the body 106.

The line normal to the curved surface of the skin of the body 106 is a straight line perpendicular to a tangent plane to the curved surface at a given point of the curved surface of the skin.

In the above-configured needle assembly 101 according to the embodiment, the front surface portion of the substrate 102, that is, the front surface 102a, has the first grooves 104a and the second grooves 104b extending, respectively, along the column direction and row direction, so as to form grooves in a matrix. The rear surface portion of the substrate 102, that is, the rear surface 102b, has the third grooves 105a and the fourth grooves 105b extending, respectively, along the column direction and row direction, so as to form grooves in a matrix. The substrate 102 is thus thinner at the groove segments formed in a matrix than in the remaining portions, allowing the substrate 102 to be easily deformed for bending.

This structure allows the substrate 102 to deform following a surface shape of the skin of the body, thus improving the ability of the needle assembly for transdermal administration to follow the skin. This, in turn, allows the vertical axis of the fine needles 103 to be displaced in a direction coinciding with the line normal to the surface of the skin of the body, thus allowing the needle assembly for transdermal administration to be highly flexible. The flexible substrate enables all the fine needles to pierce the skin uniformly, thus increasing the amount of a substance containing a medicine to be delivered into the skin.

The embodiment may be modified as appropriate in the following way. The plurality of grooves in the front surface 102a may extend in the diagonal direction of the front surface 102a, that is, a direction crossing the longitudinal and lateral directions of the front surface 102a.

The plurality of grooves in the front surface 102a may include at least two types of grooves selected from among grooves extending in the longitudinal direction, grooves extending in the lateral direction, and grooves extending in the diagonal direction.

The plurality of grooves in the rear surface 102b may extend in the diagonal direction of the rear surface 102b, that is, a direction crossing the longitudinal and lateral directions of the rear surface 102b.

The plurality of grooves in the rear surface 102b may include at least two types of grooves selected from among grooves extending in the longitudinal direction, grooves extending in the lateral direction, and grooves extending in the diagonal direction.

With reference to the accompanying drawings, description will now be given of modifications in the arrangements of the grooves formed in the substrate of the needle assembly for transdermal administration according to the present embodiment.

First Modification

Figure 4:
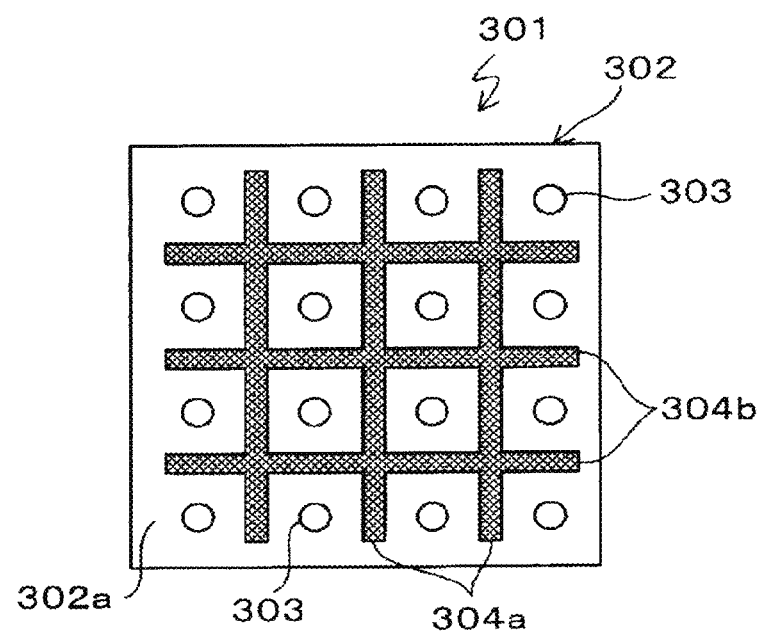
FIG. 4 is a plan view of a modification in the arrangement of the grooves in the needle assembly according to the embodiment.

A needle assembly 301 according to a modification illustrated in FIG. 4 includes a substrate 302 and a plurality of fine needles 303 projecting perpendicularly from a front surface 302a, which is one surface of the substrate 302 in a thickness direction, and arranged in a matrix at regular intervals along longitudinal and lateral directions of the front surface 302a. A group of fine needles 303 disposed in the longitudinal direction of the front surface 302a is defined as one column, and a group of fine needles 303 disposed in the lateral direction of the front surface 302a is defined as one row.

The front surface 302a includes a plurality of linear grooves 304a each formed along the column direction of fine needles 303 and located between adjacent columns of fine needles 303 so as to extend along less than the entire length of the front surface 302a in the longitudinal direction. The front surface 302a further includes a plurality of linear grooves 304b each formed along the row direction of fine needles 303 and located between adjacent rows of fine needles 303 so as to extend along less than the entire length of the front surface 302a in the lateral direction and thus to cross the grooves 304a.

The grooves 304a and 304b allow the substrate 302 to easily deform following a surface shape of the skin of the body. The lengths of the grooves 304a and 304b are designed to be less than the lengths of the front surface 302a in the longitudinal and lateral directions, respectively, so that the lengths of the grooves 304a and 304b are less than the lengths of the front surface 302a of the substrate 302 in the longitudinal and lateral directions, respectively. This configuration makes the substrate 302 suitable for a needle assembly for transdermal administration, which is used for a three-dimensionally curved skin surface of the body.

In the modification illustrated in FIG. 4, the grooves in the rear surface of the substrate 302, which is the other surface of the substrate 302 in the thickness direction, may be omitted. Alternatively, grooves similar to those in the front surface 302a of the substrate 302 may be formed such that the positions of the grooves in the front surface 302a and the rear surface are offset from each other along the row and column direction.

In other words, the positions of the grooves in the rear surface may be offset from those of the grooves in the front surface 302a as seen perpendicular to the front surface 302a. For example, the rear surface of the substrate 302 may be formed with grooves described below. Specifically, the rear surface may include a plurality of grooves extending along less than the entire length of the rear surface in the longitudinal direction, and are offset from the grooves 304a in the lateral direction, as seen perpendicular to the front surface 302a of the substrate 302. The rear surface may further include a plurality of grooves extending along less than the entire length of the rear surface in the lateral direction, and are offset from the grooves 304b in the longitudinal direction, as seen perpendicular to the front surface 302a of the substrate 302.

Second Modification

Figure 5:
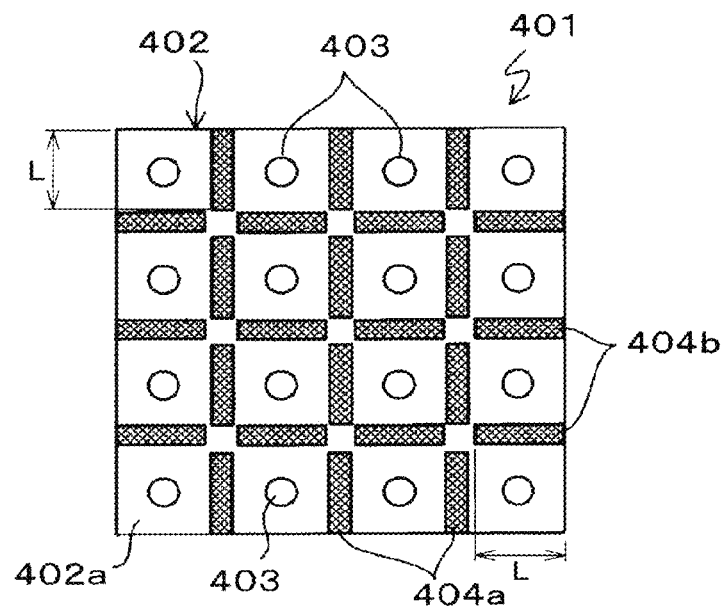
FIG. 5 is a plan view of a modification in the arrangement of the grooves in the needle assembly according to the embodiment.

The needle assembly 401 according to a modification illustrated in FIG. 5 includes a substrate 402 and a plurality of fine needles 403 projecting perpendicularly from a front surface 402a, which is one surface of the substrate 402 in a thickness direction, and arranged in a matrix at regular intervals along longitudinal and lateral directions of the front surface 402a. A group of fine needles 403 disposed in the longitudinal direction of the front surface 402a is defined as one column, and a group of fine needles 403 disposed in the lateral direction of the front surface 402a is defined as one row.

The front surface 402a has a plurality of discontinuous grooves 404a each formed along the column direction of fine needles 403 and located between adjacent columns of fine needles 403 so as to extend along the entire length of the front surface 402a in the longitudinal direction, with the discontinuous grooves 404a each separated at positions each facing fine needles 403. The front surface 402a further has a plurality of discontinuous grooves 404b each formed along the row direction of fine needles 403 and located between adjacent rows of fine needles 403 so as to extend along the entire length of the front surface 402a in the lateral direction, with the discontinuous grooves 404b each separated at positions each facing fine needles 403. The positions facing fine needles 403 refers to positions at each of which a first groove 104a of FIG. 2(a) extending in the longitudinal direction crosses a second groove 104b of FIG. 2(a) extending in the lateral direction.

The discontinuous grooves 404a and 404b allow the substrate 402 to easily deform following a surface shape of the skin of the body. The needle assembly 401 including the discontinuous grooves 404a and 404b achieves an advantageous effect similar to that exerted by the grooves illustrated in FIGS. 1-2(b).

The discontinuous grooves 404a and 404b are constituted by a plurality of groove segments. Preferably, each groove segment has a maximum length L of 200 μm or more in the front surface 402a of the substrate 402.

In the modification illustrated in FIG. 5, the grooves in the rear surface of the substrate 402, which is the other surface of the substrate 402 in the thickness direction, may be omitted. Alternatively, grooves similar to those in the front surface 402a of the substrate 402 may be formed in the rear surface, such that the positions of the grooves in the front surface 402a and the rear surface are offset from each other along the row and column direction.

For example, the rear surface of the substrate 402 may be formed with grooves described below. The rear surface of the substrate 402 may include a plurality of discontinuous grooves extending in the longitudinal direction of the rear surface and being offset from the discontinuous grooves 404a in the lateral direction, and include a plurality of discontinuous grooves extending in the lateral direction and being offset from the discontinuous grooves 404b in the longitudinal direction, as seen perpendicular to the front surface 402a of the substrate 402.

Third Modification

Figure 6:
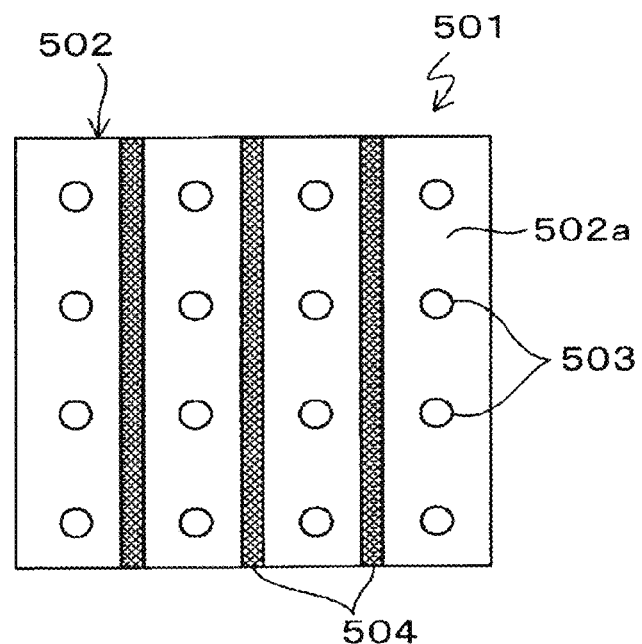
FIG. 6 is a plan view of a modification in the arrangement of the grooves in the needle assembly according to the embodiment.

The needle assembly 501 according to a modification illustrated in FIG. 6 includes a substrate 502 and a plurality of fine needles 503 projecting perpendicularly from a front surface 502a, which is one surface of the substrate 502 in a thickness direction, and arranged in a matrix at regular intervals along longitudinal and lateral directions of the front surface 502a. With a group of fine needles 503 disposed in the longitudinal direction of the front surface 502a being defined as one column, the front surface 502a includes a plurality of grooves 504 each formed along the column direction of fine needles 503 and located between adjacent columns of fine needles 503 so as to extend along the entire length of the front surface 502a in the longitudinal direction.

The grooves 504 allow the substrate 502 to easily deform following a surface shape of the skin of the body. The needle assembly 501 including the grooves 504 achieves an advantageous effect similar to that exerted by the grooves illustrated in FIGS. 1-2(b).

In the modification illustrated in FIG. 6, the grooves in the rear surface of the substrate 502, which is the other surface of the substrate 502 in the thickness direction, may be omitted. Alternatively, grooves similar to those in the front surface 502a of the substrate 502 may be formed such that the positions of the grooves in the front surface 502a and the rear surface are offset from each other along the row direction.

For example, the rear surface of the substrate 502 may include a plurality of grooves extending in the longitudinal direction of the rear surface and being offset from the grooves 504 in the lateral direction, as seen perpendicular to the front surface 502a of the substrate 502.

Fourth Modification

Figure 7:
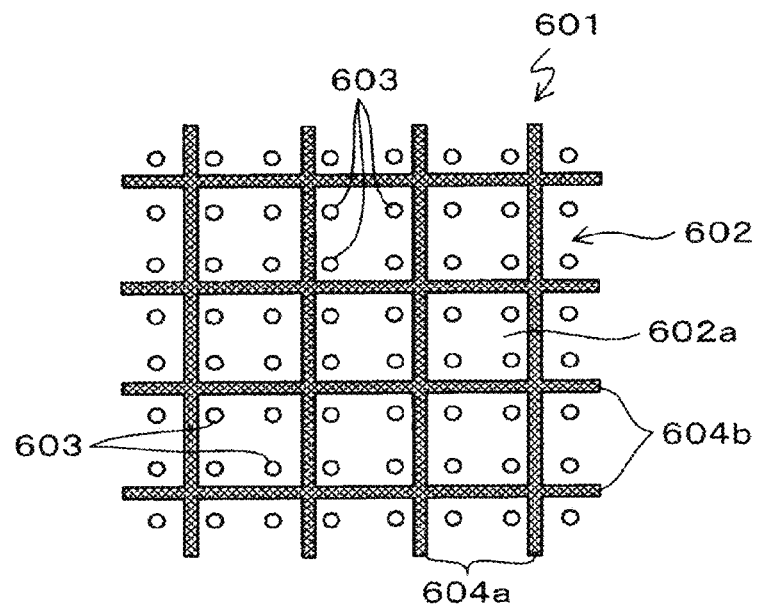
FIG. 7 is a plan view of a modification in the arrangement of the grooves in the needle assembly according to the embodiment.

The needle assembly 601 according to a modification illustrated in FIG. 7 includes a substrate 602 and a plurality of fine needles 603 projecting perpendicularly from the front surface 602a, which is one surface of the substrate 602 in a thickness direction, and arranged in a matrix at regular intervals along longitudinal and lateral directions of the front surface 602a. A group of fine needles 603 disposed in the longitudinal direction of the front surface 602a is defined as one column, and a group of fine needles 603 disposed in the lateral direction of the front surface 602a is defined as one row.

The front surface 602a includes a plurality of linear grooves 604a each formed along the column direction of fine needles 603 and located between adjacent columns of fine needles 603 so as to extend in the longitudinal direction of the front surface 602a, so that adjacent linear grooves 604a are spaced apart from each other by a distance corresponding to 2 spaces, which corresponds to a length along the row direction of two adjacent columns of fine needles 603. The front surface 602a further includes a plurality of linear grooves 604b each formed along the row direction of fine needles 603 and located between adjacent rows of fine needles 603 so as to extend in the lateral direction of the front surface 602a, so that adjacent linear grooves 604b are spaced apart from each other by a distance corresponding to 2 spaces, which corresponds to a length along the column direction of two adjacent rows of fine needles 603.

That is, in the front surface 602a of the substrate 602, each groove 604a extending in the longitudinal direction of the substrate 602 is disposed in a gap between two columns of fine needles 603 adjacent along the row, so that one groove 604a is disposed every two columns. Each groove 604b extending in the lateral direction of the substrate 602 is disposed in a gap between two rows of fine needles 603 adjacent along the column direction, so that one groove 604b is disposed every two rows.

The grooves 604a and 604b allow the substrate 602 to easily deform following a surface shape of the skin of the body. The needle assembly 601 including the grooves 604a and 604b achieves an advantageous effect similar to that exerted by the grooves illustrated in FIGS. 1-2(b).

In the modification illustrated in FIG. 7, the grooves in the rear surface of the substrate 602, which is the other surface of the substrate 602 in the thickness direction, may be omitted. Alternatively, grooves similar to those in the front surface 602a of the substrate 602 may be formed in the rear surface, such that the positions of the grooves in the front surface 602a and the rear surface are offset from each other along the row and column direction.

For example, the rear surface of the substrate 602 may be formed with grooves described below. Specifically, the rear surface of the substrate 602 may include a plurality of grooves extending in the longitudinal direction of the rear surface and being offset from the grooves 604a in the lateral direction, and include a plurality of grooves extending in the lateral direction and being offset from the grooves 604b in the longitudinal direction, as seen perpendicular to the front surface 602a of the substrate 602.

Fifth Modification

Figure 8:
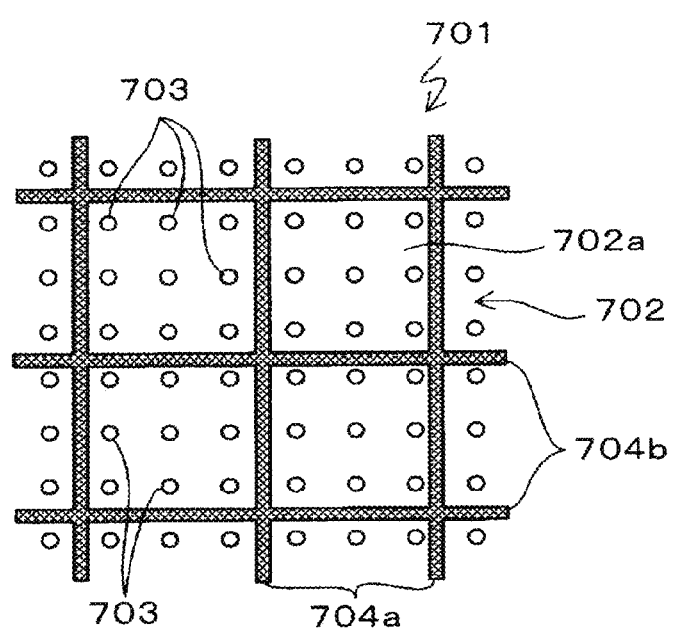
FIG. 8 is a plan view of a modification in the arrangement of the grooves in the needle assembly according to the embodiment.

A needle assembly 701 according to a modification illustrated in FIG. 8 includes a substrate 702 and a plurality of fine needles 703 projecting perpendicularly from a front surface 702a, which is one surface of the substrate 702 in a thickness direction, and arranged in a matrix at regular intervals along longitudinal and lateral directions of the front surface 702a. A group of fine needles 703 disposed in the longitudinal direction of the front surface 702a is defined as one column, and a group of fine needles 703 disposed in the lateral direction of the front surface 702a is defined as one row.

The front surface 702a includes a plurality of linear grooves 704a each formed along the column direction of fine needles 703 and located between adjacent columns of fine needles 703 so as to extend in the longitudinal direction of the front surface 702a, so that adjacent linear grooves 704a are spaced apart from each other by a distance corresponding to 3 spaces, which corresponds to a length along the row direction of three adjacent columns of fine needles 703. The front surface 702a further includes a plurality of linear grooves 704b each formed along the row direction of fine needles 703 and located between adjacent rows of fine needles 703 so as to extend in the lateral direction of the front surface 702a, so that adjacent linear grooves 704b are spaced apart from each other by a distance corresponding to 3 spaces, which corresponds to a length along the column direction of three adjacent rows of fine needles 603.

That is, in the front surface 702a of the substrate 702, each groove 704a extending in the longitudinal direction of the substrate 702 is disposed in a gap between two columns of fine needles 703 adjacent along the row direction, so that one groove 704a is disposed every three columns. Each groove 704b extending in the lateral direction of the substrate 702 is disposed in a gap between two rows of fine needles 703 adjacent along the column direction, so that one groove 704b is disposed every three rows.

The fifth modification in the arrangement of the grooves achieves an effect similar to that exerted by the grooves illustrated in FIGS. 1-2(b).

In the modification illustrated in FIG. 8, the grooves in the rear surface of the substrate 702, which is the other surface of the substrate 702 in the thickness direction, may be omitted. Alternatively, grooves similar to those in the front surface 702a of the substrate 702 may be formed such that the positions of the grooves in the front surface 702a and the rear surface are offset from each other along the row and column direction.

For example, the rear surface of the substrate 702 may be formed with grooves described below. Specifically, the rear surface of the substrate 702 may include a plurality of grooves extending in the longitudinal direction of the rear surface and being offset from the grooves 704a in the lateral direction, and include a plurality of grooves extending in the lateral direction and being offset from the grooves 704b in the longitudinal direction, as seen perpendicular to the front surface 702a of the substrate 702.

With reference to the accompanying drawings, description will now be given of other exemplary arrangements of the grooves in the needle assembly for transdermal administration according to the present embodiment.

Second Exemplary Arrangement

Figure 9A:
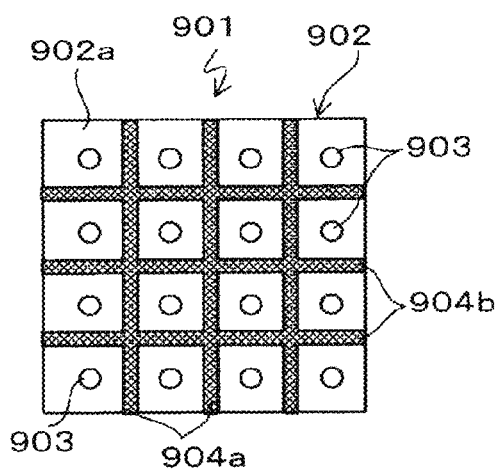
FIGS. 9(a) and 9(b) are plan views of the needle assembly according to the embodiment.
Figure 9B:
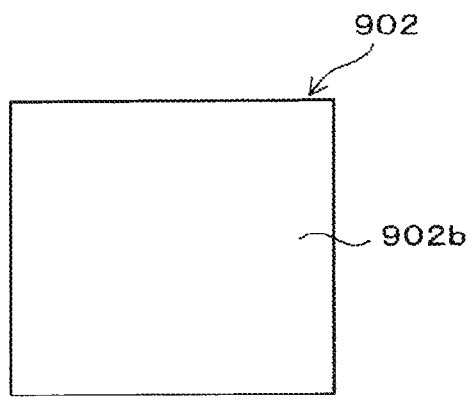

As with the exemplary arrangement of FIG. 2 (a), a needle assembly 901 according to an exemplary arrangement of FIG. 9 includes, as illustrated in FIG. 9 (a), a substrate 902 and a plurality of fine needles 903 projecting perpendicularly from a front surface 902a of the substrate 902 and arranged in a matrix at regular intervals along longitudinal and lateral directions of the front surface 902a. The front surface 902a includes a plurality of linear grooves 904a each formed along the column direction of fine needles 903 and located between adjacent columns of fine needles 903 disposed in the longitudinal direction so as to extend along the entire length of the substrate 902 in the longitudinal direction. The front surface 902a further includes a plurality of linear grooves 904b each formed along the row direction of fine needles 903 and located between adjacent rows of fine needles 903 disposed in the lateral direction so as to extend along the entire length of the front surface 902a in the lateral direction and thus to cross the grooves 904a.

As illustrated in FIG. 9 (b), the rear surface 902b of the substrate 902 is not formed with grooves that allow the substrate 902 to easily deform following a surface shape of the skin of the body, unlike FIG. 2 (b).

The needle assembly according to the second exemplary arrangement achieves an effect similar to that exerted by the grooves illustrated in FIGS. 1-2(b).

Third Exemplary Arrangement

Figure 10A:
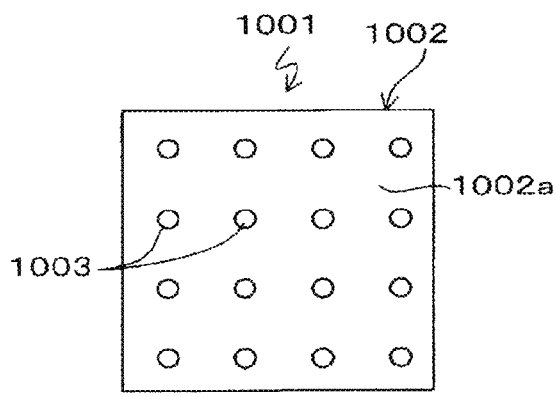
FIGS. 10(a) and 10(b) are plan views of the needle assembly according to the embodiment.
Figure 10B:
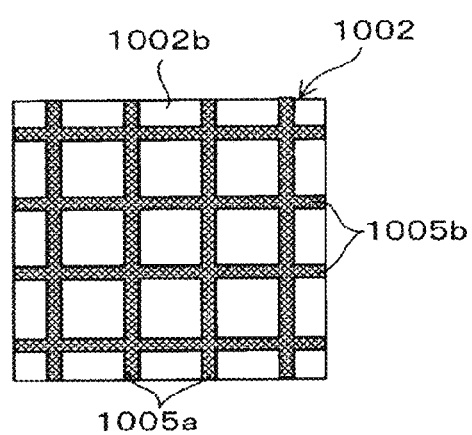

As illustrated in FIG. 10 (a), a needle assembly 1001 according to an exemplary arrangement of FIG. 10 includes a substrate 1002 and a plurality of fine needles 1003 projecting perpendicularly from a front surface 1002a of the substrate 1002 and arranged in a matrix at regular intervals along longitudinal and lateral directions of the front surface 1002a.

As illustrated in FIG. 10 (b) and as with the exemplary arrangement of FIG. 2 (b), a rear surface 1002b of the substrate 1002 includes a plurality of linear third grooves 1005a each formed along the column direction of fine needles 1003 and extending along the entire length of the rear surface 1002b in the longitudinal direction. The rear surface 1002b of the substrate 1002 further includes a plurality of linear third grooves 1005b each formed along the row direction of fine needles 1003 and extending along the entire length of the substrate 1002 in the lateral direction so as to cross the grooves 1005a.

The needle assembly according to the third exemplary arrangement achieves an effect similar to that exerted by the grooves illustrated in FIGS. 1-2(b).

Fourth Exemplary Arrangement

Figure 11A:
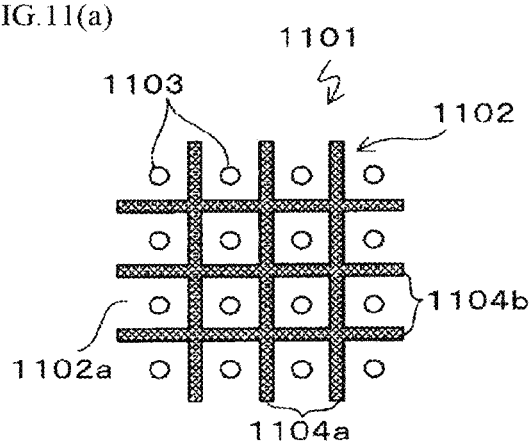
FIGS. 11(a) and 11(b) are plan views of the needle assembly according to the embodiment.
Figure 11B:
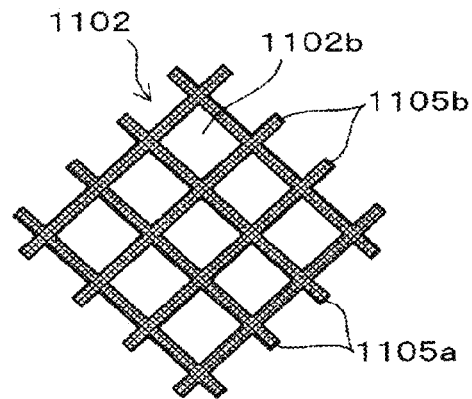

As illustrated in FIG. 11 (a), a needle assembly 1101 according to an exemplary arrangement of FIG. 11 includes a substrate 1102 and a plurality of fine needles 1103 projecting perpendicularly from a front surface 1102a of the substrate 1102 and arranged in a matrix at regular intervals along longitudinal and lateral directions of the front surface 1102a. The front surface 1102a includes a plurality of linear grooves 1104a each formed along the column direction of fine needles 1103 and located between adjacent columns of fine needles 1103 disposed in the longitudinal direction so as to extend along the entire length of the substrate 1102 in the longitudinal direction. The front surface 1102a further includes a plurality of linear grooves 1104b each formed along the row direction of fine needles 1103 and located between adjacent rows of fine needles 1103 disposed in the lateral direction so as to extend along the entire length of the front surface 1102a in the lateral direction and thus to cross the grooves 1104a.

As illustrated in FIG. 11 (b), a rear surface 1102b of the substrate 1102 includes a plurality of first grooves 1105a each extending in a diagonal direction at an angle of 45° from upper left to lower right relative to the grooves 1104a in the row direction and the grooves 1104b in the column direction, and disposed parallel to each other at regular intervals in a direction perpendicular to the diagonal direction. The rear surface 1102b includes a plurality of second grooves 1105b each extending in a direction perpendicular to the first grooves 1105a and disposed parallel to each other at regular intervals in the perpendicular direction. Thus, the rear surface 1102b of the substrate 1102 includes grooves formed in a matrix.

That is, the rear surface 1102b includes a plurality of first grooves 1105a each extending in the diagonal direction at an angle of 45° relative to the longitudinal and lateral directions and formed at regular intervals in the direction perpendicular to the diagonal direction as seen perpendicular to the front surface 1102a of the substrate 1102. The rear surface 1102b includes a plurality of second grooves 1105b each extending in the direction perpendicular to the first grooves 1105a and formed at regular intervals along the first grooves 1105a.

The needle assembly according to the fourth exemplary arrangement achieves an effect similar to that exerted by the grooves illustrated in FIGS. 1-2(b).

Fifth Exemplary Arrangement

Figure 12A:
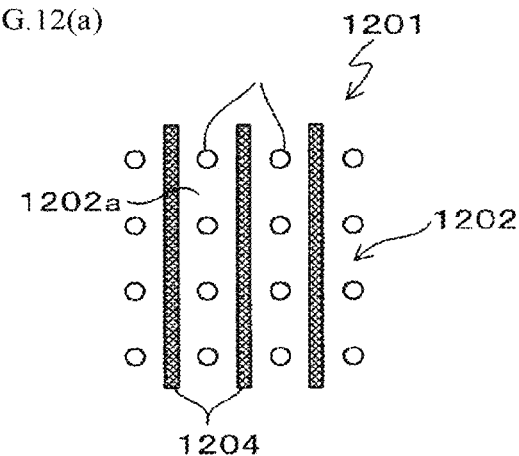
FIGS. 12(a) and 12(b) are plan views of the needle assembly according to the embodiment.
Figure 12B:
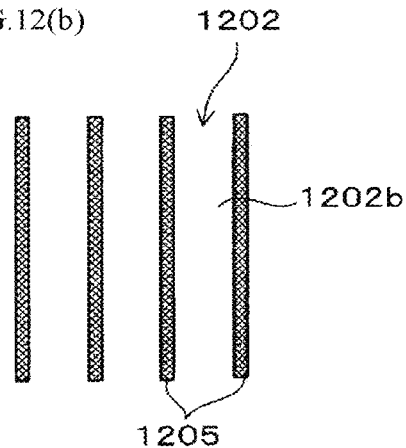

As illustrated in FIG. 12 (a), a needle assembly 1201 according to an exemplary arrangement of FIG. 12 includes a substrate 1202 and a plurality of fine needles 1203 projecting perpendicularly from a front surface 1202a of the substrate 1202 and arranged in a matrix at regular intervals along longitudinal and lateral directions of the front surface 1202a. With a group of fine needles 1203 disposed in the longitudinal direction of the front surface 1202a being defined as one column, the front surface 1202a includes a plurality of grooves 1204 each formed along the column direction of fine needles 1203 and located between adjacent columns of fine needles 1203 so as to extend in the longitudinal direction of the front surface 1202a.

As illustrated in FIG. 12 (b), the rear surface 1202b of the substrate 1202 includes a plurality of grooves 1205 each formed at a portion corresponding to a column of fine needles 1203 and each extending in the longitudinal direction of the rear surface 1202b along the column direction of fine needles 1203. That is, the rear surface 1202b of the substrate 1202 includes the grooves 1205 each formed at a position corresponding to a column of fine needles 1203 and extending in the longitudinal direction as seen perpendicular to the front surface 1202a of the substrate 1202.

The needle assembly according to the fifth exemplary arrangement achieves an effect similar to that exerted by the grooves illustrated in FIGS. 1-2(b).

Sixth Exemplary Arrangement

Figure 13A:
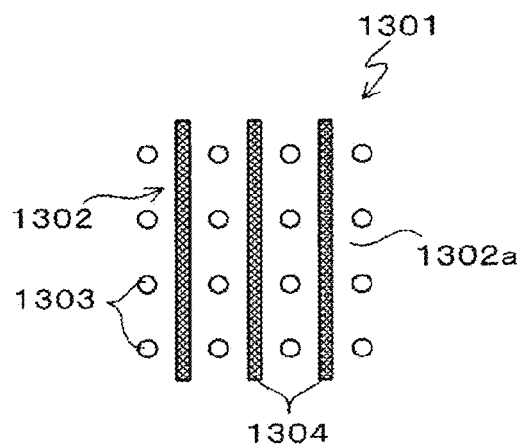
FIGS. 13(a) and 13(b) are plan views of the needle assembly according to the embodiment.
Figure 13B:
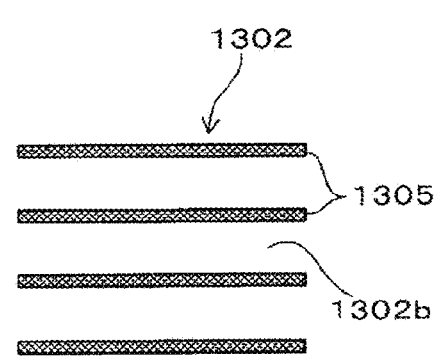
Figure 14A:
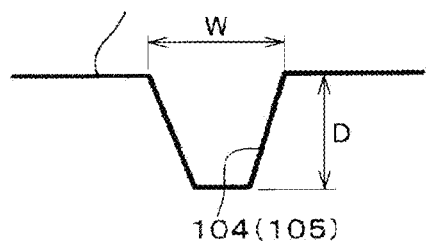
FIGS. 14(a)-14(d) are exemplary diagrams each illustrating a cross section of the grooves in the needle assembly according to the embodiment.
Figure 14B:
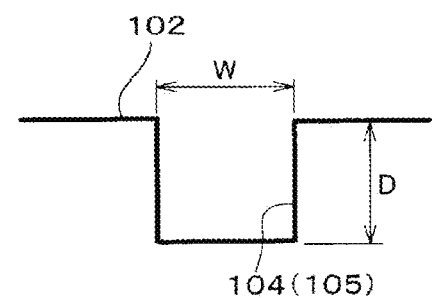
Figure 14C:
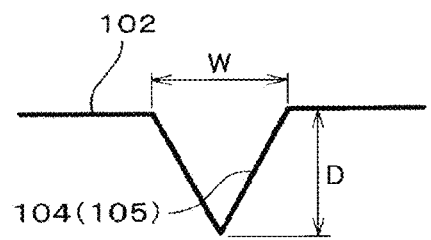
Figure 14D:
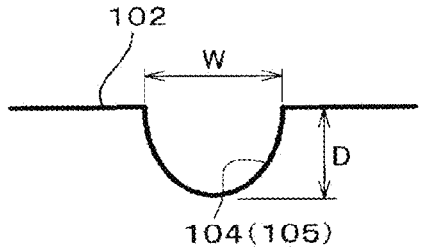

As illustrated in FIG. 13 (a), a needle assembly 1301 according to an exemplary arrangement of FIGS. 13(a) and 13(b) includes a substrate 1302 and a plurality of fine needles 1303 projecting perpendicularly from a front surface 1302a of the substrate 1302 and arranged in a matrix at regular intervals along longitudinal and lateral directions of the front surface 1302a. With a group of fine needles 1303 disposed in the longitudinal direction of the front surface 1302a being defined as one column, the front surface 1302a includes a plurality of grooves 1304 each formed along the column direction of fine needles 1303 and located between adjacent columns of fine needles 1303 so as to extend in the longitudinal direction of the front surface 1302a.

As illustrated in FIG. 13 (b), a rear surface 1302b of the substrate 1302 includes a plurality of grooves 1305 each formed at a portion corresponding to a row of fine needles 1303 and each extending in the lateral direction of the rear surface 1302b along the row direction of fine needles 1303 so as to be perpendicular to the fine needles 1304 in the front surface. That is, the rear surface 1302b of the substrate 1302 includes grooves 1305 each formed at a position corresponding to a row of fine needles 1303 and extending in the lateral direction as seen perpendicular to the front surface 1302a of the substrate 1302.

The needle assembly according to the sixth exemplary arrangement achieves an effect similar to that exerted by the grooves illustrated in FIGS. 1-2(b).

With reference to FIGS. 15(a)-15(d), description will now be given of a method of producing the needle assembly for transdermal administration according to the present embodiment.

The method of producing the needle assembly according to the present embodiment includes a step of preparing an original plate, a step of preparing a reproduction plate having a reversed pattern of the original plate, a step of forming a needle assembly, using the reproduction plate, and a step of releasing the needle assembly from the reproduction plate after the needle assembly has been cured.

<Step of Preparing Original Plate>

An original plate can be formed using an appropriate, known micromachining technique. For example, an original plate of the needle assembly for transdermal administration may be produced by (1) using micromachining such as grinding or cutting to a substrate, or (2) using micromachining such as lithography or etching.

The material used for the original plate can be selected according to the adopted processing method. For example, a silicon substrate can be used when the original plate is produced by grinding, and a brass substrate can be used when the original plate is produced by cutting.

As illustrated in FIG. 15 (a), an original plate 201 includes a substrate-forming portion 201a for forming a substrate of a needle assembly for transdermal administration, and, in the upper surface of the forming substrate portion 201a, a needle-forming portion 201b for forming a fine needle of the needle assembly for transdermal administration. The original plate 201 further includes a groove-forming portion 201c for forming a groove that allows the substrate of the needle assembly for transdermal administration to deform following a surface shape of the skin of the body, in the upper surface of the substrate-forming portion 201a.

The groove-forming portion 201c extends linearly in at least one direction between adjacent needle-forming portions 201b. The groove-forming portions 201c can be formed using the method of producing the original plate. Each groove-forming portion 201c formed between needle-forming portions 201b may have any width. However, considering workability, for example, the width of the groove-forming portion 201c preferably ranges from 50 μm to 1000 μm, inclusive, and more preferably, from 100 μm to 300 μm, inclusive. Each groove-forming portion 201c formed in a substrate-forming portion 201a may have any depth. However, considering workability, for example, the depth of the groove-forming portion 201c preferably ranges from 50 μm to 1000 μm, inclusive, and more preferably, from 100 μm to 300 μm, inclusive.

<Step of Preparing Reproduction Plate>

A reproduction plate can be formed using an appropriate, known micromachining technique. Specifically, after the original plate 201 has been formed, the upper surface of the original plate 201 is filled with a filling material for forming a reproduction plate, and then the filling material is released from the original plate 201, to form a reproduction plate 202 illustrated in FIG. 15 (b). As illustrated in FIG. 15 (b), the upper surface of the reproduction plate 202 includes a flat portion 202a corresponding to the substrate-forming portion 201a of the original plate 201, a recess 202b corresponding to the needle-forming portion 201b of the original plate 201, and a linear projection 202c corresponding to the groove-forming portion 201c of the original plate 201.

Any filling material can be selected for use in the formation of the reproduction plate 202 as long as it allows the reproduction plate 202 to have shape followability, durability, and releasability, and thus to function as a reproduction plate. For example, nickel and a thermosetting silicone resin may be used. When nickel is selected, plating, physical vapor deposition (PVD), or chemical vapor deposition (CVD) can be used as a method of forming the filling material.

<Step of Forming Needle Assembly using Reproduction Plate>

As illustrated in FIG. 15 (c), a polymer material 203 is placed on the surface of the reproduction plate 202, the surface including the flat portion 202a, recess 202b, and projection 202c. Then, the polymer material 203 is melted by heating, and the melted polymer material 203 is pressed with a press 204, followed by curing to form a needle assembly as a molded product.

As illustrated in FIG. 15 (c), the press 204 includes a flat surface portion 204a facing the flat portion 202a of the reproduction plate 202, and a projection 204b formed on the flat surface portion 204a so as to extend in a direction coinciding with or perpendicular to a direction in which the recess 202b of the reproduction plate 202 extends. As illustrated in FIG. 15 (d), the projection 204b is used for forming grooves 207a and 207b on, respectively, a front surface 205a of a needle assembly 205 as a molded product and a rear surface 205b, which is opposite to the front surface 205a. The forming grooves 207a and 207b allow a substrate to deform following a surface shape of the skin of the body.

Nonlimiting examples of the polymer material 203 for forming a needle assembly as a molded product include biocompatible materials such as a medical silicone resin, and thermoplastic polymer materials such as polyglycolic acid, polylactic acid, and polycarbonate. These materials may be used to form a needle assembly applicable to the body. The use of a biocompatible material allows the needle assembly to be harmless even if a needle portion breaks off and remains in the body. The polymer material 203 may be a thermoplastic polymer material such as polyethylene resin, polypropylene resin, cyclic polyolefin resin, epoxy resin, polyamide resin, phenol resin, polystyrene resin, polycaprolactone resin, acrylic resin, urethane resin, aromatic polyether ketone, and epoxy resin. Such a thermoplastic polymer material is preferably used as the material for the needle assembly of the present embodiment.

Preferable methods of filling the reproduction plate 202 with the polymer material 203 include, but are not limited to, imprinting, hot embossing, and injection molding.

Preferably, the reproduction plate 202 is filled with a polymer material through pressing using a press or a mold. The material of the press can be selected as appropriate considering durability or workability. For example, when durability is considered, SUS303 can be used; when workability is considered, A5052 can be used.

Figure 15A:
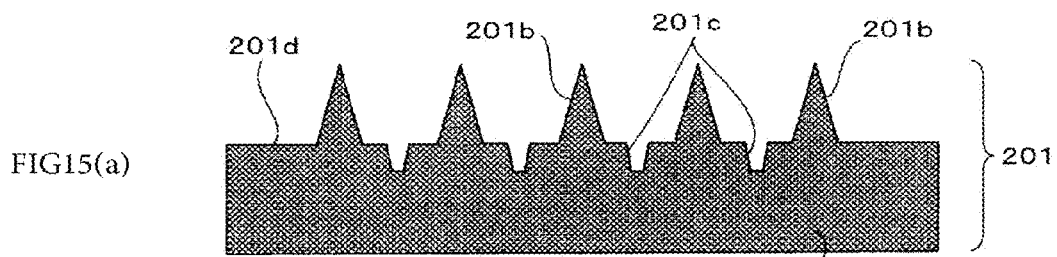
FIGS. 15(a)-15(d) are diagrams each illustrating a process for producing a needle assembly, according to a method of producing the needle assembly according to the embodiment.
Figure 15B:
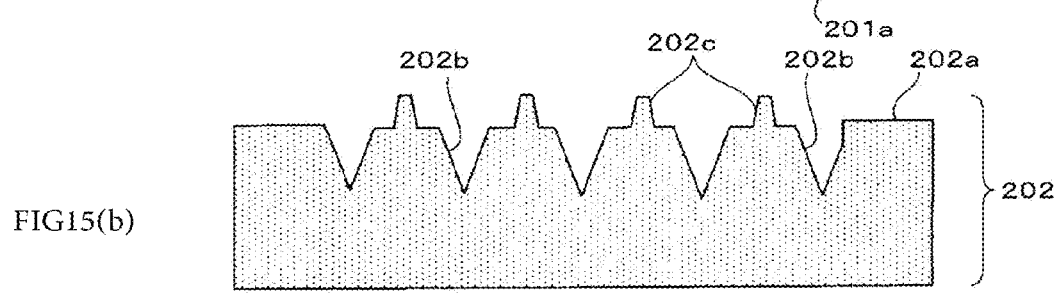
Figure 15C:
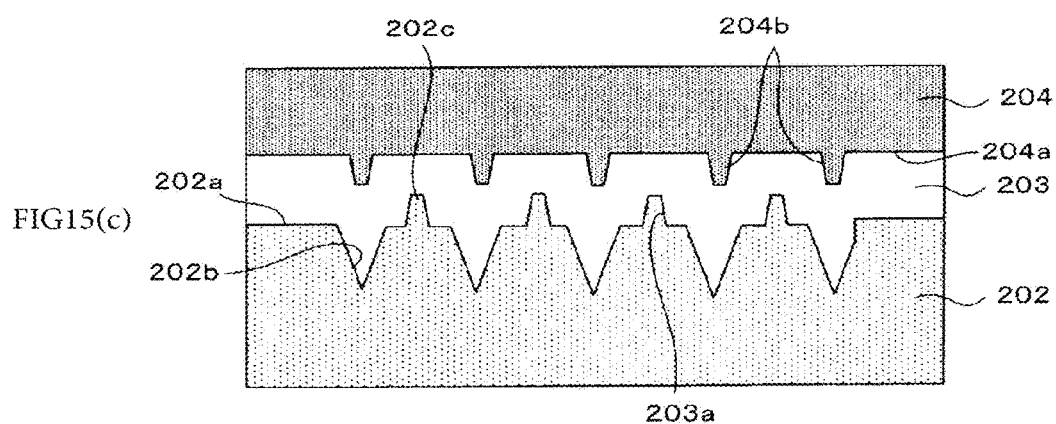
Figure 15D:
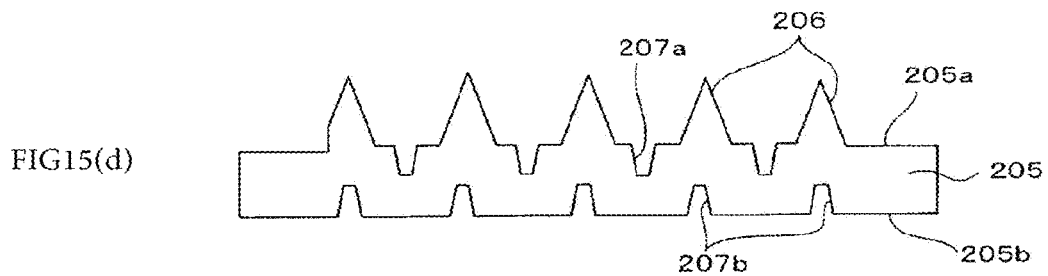

Although the press 204 of FIG. 15(c) is flat, a roller-shaped press can be used. In the present embodiment, the needle assembly can be produced through roll-to-roll processing, using a roller-shaped reproduction plate and a roller-shaped press.

The polymer material filled in the reproduction plate is cured by cooling. The polymer material can be cured using any method. For example, the reproduction plate may be blown with air and cooled, so that the polymer material is indirectly cured.

The material for forming the needle assembly of the present embodiment may be a water-soluble material. Examples of the water-soluble material include water-soluble polymer materials and polysaccharides. Nonlimiting examples of the water-soluble polymer materials and polysaccharides include chitosan, chitosan succinamide, hydroxypropyl cellulose (HPC), carboxymethyl cellulose (CMC), sodium chondroitin sulfate, dextran, curdlan, trehalose, sucrose, gelatin, collagen, pullulan, pectin, alginates, starch, methyl cellulose, hydroxypropylmethyl cellulose (HPMC), polyvinyl alcohol (PVA), polyacrylic acid polymer, polyacrylamide (PAM), and polyethylene oxide (PEO).

When a water-soluble material is used as the material for forming the needle assembly of the present embodiment, a method of producing the needle assembly may involve dissolving or dispersing the material for forming the needle assembly in a solvent such as water, to prepare a liquid material, and filling the liquid material in a reproduction plate. In that case, after the liquid material has been filled in the reproduction plate, the liquid material may be heated to dry and remove the solvent, followed by curing. Thus, the needle assembly can be produced.

<Step of Removing Cured Needle Assembly>

The needle assembly formed of the polymer material that has been cured by cooling is released from the reproduction plate to obtain a needle body. The needle assembly can be released by peeling using physical peeling force, or selective etching, for example.

To improve releasability of the needle assembly as a molded product from the reproduction plate, a release layer for enhancing the effect of releasing may be formed on a surface of the reproduction plate before a polymer material is filled in the reproduction plate. The release layer may be made of a fluoride resin.

The release layer can be preferably formed using a method of forming a thin film, such as PVD, CVD, spin coating, or dip coating.

The outline of the method of producing the needle body of the present embodiment has been described. However, other methods applicable to the respective steps may be used instead.

EXAMPLE

Example 1

With reference to FIGS. 15 (a) to (d), a method of producing the needle assembly of the present embodiment will be described by way of an example. A ceramics substrate having a thickness of 5 mm was used as a substrate for forming an original plate.

The substrate was machined with a two-lip ball end mill having a 0.01 mm radius ball. The ball end mill as a cutting tool was mounted to an NC controlled XYZ-axis milling machine. The cutting depth of the cutting tool was increased to deeply carve a needle body as the cutting tool was revolved from the center of the needle body toward its perimeter, so that the needle body had a conical portion.

The number of revolutions of the ball end mill was set to 50000 rpm, and a feed rate was set to 0.1 mm/s. The cones formed by the machining were designed to have a bottom surface diameter of 280 µm, a pitch of 500 µm, and a depth of 450 µm. Portions with no fine needles were each uniformly cut to have a depth of 450 µm, so that vertexes of the fine needles had the greatest height on the substrate-forming portion 201a. Likewise, as with the exemplary arrangement of FIG. 2 (a), groove-forming portions 201c each having a width of 150 µm and a depth of 100 µm were formed in a longitudinal direction and a lateral direction, perpendicular to the longitudinal direction, of a front surface 201d of the substrate-forming portion 201a, with the front surface 201d being exposed between adjacent needle-forming portions 201b. As a result of the process, an original plate 201 was produced (FIG. 15 (a)).

The original plate 201 produced as described above was observed using a scanning electron microscope (SEM). As a result of the observation, the formation of needle-forming portions 201b and groove-forming portions 201c were confirmed. The needle-forming portions 201b each were a conical projection having a width of 280 µm at its base, a height of 445 µm, and a tip angle of 35°. The groove-forming portions 201c each had a width of 150 µm and a depth of 100 µm. Further, it was confirmed that 25 needle-forming portions 201b were formed in a square lattice with a pitch of 500 µm.

Then a silicone resin as a filling material was filled in the original plate 201, and the filling material was subjected to thermosetting treatment at 100° C. for 1 hour in a clean oven. Then, the filling material was released from the original plate to produce the reproduction plate 202 formed of the silicone resin (FIG. 15 (b)).

Then, a needle assembly for transdermal administration was produced by imprinting. Polyglycolic acid as the polymer material 203 was placed on the reproduction plate 202, and then the polymer material was heated and melted using a hot plate set to 250° C. Then, the polymer material 203 was pressed with the press 204 so as to be filled in the reproduction plate 202. The material of the press 204 was SUS 303. The projection 202c of the reproduction plate 202 allows the front surface of the polymer material 203, which was polyglycolic acid, to be formed with grooves 203a having a width of 150 µm and a depth of 100 µm in a longitudinal direction and a lateral direction, perpendicular to the longitudinal direction, of the front surface (FIG. 15 (c)).

Lastly, the polymer material 203 was released from the reproduction plate 202. As a result of the SEM observation, the formation of a needle assembly for transdermal administration 205 was confirmed. The needle assembly 205 included conical fine needles 206 made of polyglycolic acid and having a diameter of 280 µm at its base, a height of 445 µm, and a tip angle of 35°. It was confirmed that the front surface 205a of the needle assembly 205 was formed with grooves 207a each positioned between adjacent fine needles 206 and having a width of 150 µm and a depth of 100 µm. The grooves 207a were formed in a longitudinal direction and a lateral direction, perpendicular to the longitudinal direction, of the front surface 205a. The rear surface 205b of the needle assembly 205 was also confirmed to be formed with grooves 207b each having a width of 150 µm and a depth of 100 µm in a longitudinal direction and a lateral direction, perpendicular to the longitudinal direction, of the front surface 205a. The fine needles 206, which were 25 in all, were arranged in a square lattice with a pitch of 495 µm (FIG. 15 (d)). The size of the substrate of the needle assembly 205 was 5 cm×5 cm, and its thickness was 500 µm.

To confirm that the needle assembly for transdermal administration according to the present embodiment increases the amount of medicines delivered, a needle assembly for transdermal administration was additionally prepared which was of the same design except that it had no grooves, and the two types of needle assemblies for transdermal administration were pierced into a swine skin, to compare the number of piercing scars. To observe the piercing of fine needles into the swine skin, these fine needles were stained with a blue ink in advance. The test showed that 25 piercing scars equal in number to the fine needles were formed in the swine skin into which the needle assembly with grooves was pierced, whereas 18 piercing scars were formed in a swine skin into which the needle assembly without grooves was pierced. These results confirmed that the present embodiment increases the amount of medicines delivered.

The needle assembly for transdermal administration according to the present embodiment achieves greater effects as the substrate of the needle assembly increases in size. This is because as the substrate of the needle assembly increases in size, greater flexibility is required for the needle assembly to allow the substrate to follow the skin. The needle assembly according to the present embodiment is preferably applied to a needle assembly having a substrate which is 4 cm$^2$ or more.

The needle assembly for transdermal administration according to the present embodiment achieves greater effects as the substrate of the needle assembly increases in thickness. This is because as the substrate of the needle assembly increases in thickness, flexibility decreases in the needle assembly. The needle assembly according to the present embodiment is preferably applied to a needle assembly having a substrate with a thickness of 200 μm or more.

The needle assembly for transdermal administration according to the present embodiment achieves greater effects when the substrate and fine needles of the needle assembly are made of a thermoplastic polymer material. This is because as the size of the substrate increases, flexibility decreases in the needle assembly formed of a thermoplastic polymer material.

When a needle body having grooved needle portions is used as described in PTL 4, it is difficult for all the needles of the needle body to pierce the skin uniformly, rendering such a needle body inappropriate for assisting the delivery of medicines into the body. This difficulty comes from the fact that the skin has an uneven surface, and a substrate of the needle body is insufficiently flexible for the needle body to pierce the skin.

An aspect of the present invention is to provide a needle assembly for transdermal administration, in which a substrate having a plurality of fine needles capable of piercing the skin is formed to flexibly deform following a surface shape of the skin of the body, and a method of producing the same.

To overcome the problem, the needle assembly for transdermal administration includes a substrate having a first surface and a second surface opposite to the first surface, and a plurality of fine needles projecting perpendicularly from the first surface. The substrate has a plurality of grooves formed in at least one of the first surface and the second surface. The plurality of grooves are formed to allow the substrate to deform following a surface shape of the skin of the body, such that axes of the fine needles are each displaced in a direction coinciding with a direction of the line normal to the surface of the skin of the body.

In the needle assembly for transdermal administration, the fine needles are arranged in a matrix at regular intervals along longitudinal and lateral directions of the first surface. The plurality of grooves include a plurality of grooves formed in the first surface so as to extend in a first direction between adjacent ones of the fine needles, and to be arranged in a second direction perpendicular to the first direction. The first direction preferably includes at least one of the longitudinal direction, the lateral direction, and a diagonal direction of the first surface.

In the needle assembly for transdermal administration, the plurality of grooves include a plurality of grooves formed in the second surface so as to extend in a third direction, and to be arranged in a fourth direction perpendicular to the third direction. The third direction includes at least one of a longitudinal direction, a lateral direction, and a diagonal direction of the second surface. The positions of the plurality of grooves in the second surface may be offset from the positions of the grooves in the first surface as seen perpendicular to the first surface.

In the needle assembly for transdermal administration, the plurality of grooves may include one type of grooves selected from among grooves each having a trapezoidal cross section, grooves each having a rectangular cross section, grooves each having a triangular cross section, grooves each having a semicircular cross section, and grooves each having a semielliptical cross section, the cross sections being perpendicular to a direction in which the grooves extend.

To overcome the problem, a method of producing the needle assembly for transdermal administration according to an embodiment of the present invention includes a substrate and a plurality of fine needles formed in one surface of the substrate so as to project perpendicularly from the one surface. This method includes a step of producing an original plate of the needle assembly for transdermal administration, such that the original plate includes a substrate-forming portion for forming the substrate, and includes, in the upper surface of the substrate-forming portion, a needle-forming portion for forming the fine needles and a groove-forming portion for forming a groove that allows the substrate to deform following a surface shape of the skin of the body, and a step of forming a reproduction plate that includes a flat portion corresponding to the substrate-forming portion, a recess corresponding to the needle-forming portion, and a linear projection corresponding to the groove, based on the original plate. The method of producing the needle assembly for transdermal administration includes a step of heating a polymer material to melt the polymer material after the polymer material has been placed on a surface of the reproduction plate, the surface including the flat portion, the recess, and the projection, a step of pressing the polymer material melted in the heating step, using a press including both a flat surface portion facing the flat portion and a projection formed in the flat surface portion so as to extend in a direction coinciding with or perpendicular to a direction in which the groove-forming portion extends, followed by curing to form a needle assembly, and a step of releasing the cured needle assembly from the reproduction plate.

According to the method of producing the needle assembly for transdermal administration, the polymer material is preferably a biocompatible, thermoplastic resin.

According to the needle body of the present invention and a method of producing the same, a substrate having a plurality of fine needles capable of piercing the skin flexibly deforms following a surface shape of the skin of the body.

INDUSTRIAL APPLICABILITY

Besides medical fields, the method of producing the needle assembly for transdermal administration can be applied in a variety of fields in which a needle assembly for transdermal administration is used. For example, the method is useful in producing a needle assembly for transdermal administration for use in drug development, cosmetics, and beauty applications.

REFERENCE SIGNS LIST

101: Needle assembly for transdermal administration, 102: Substrate, 103: Fine needle, 104: First groove, 105: Second groove, 104*a*: First groove, 104*b*: Second groove, 105*a*: Third groove, 105*b*: Fourth groove, 201: Original plate, 202: Reproduction plate, 203: Polymer material, 204: Press, 205: Needle assembly for transdermal administration Obviously, numerous modifications and variations of the present invention are possible in light of the above teachings. It is therefore to be understood that within the scope of the appended claims, the invention may be practiced otherwise than as specifically described herein.

What is claimed is:

1. A needle assembly for transdermal administration, comprising:
    a substrate having a first surface and a second surface opposite to the first surface; and
    a plurality of fine needles projecting perpendicularly from the first surface and positioned in a matrix on the first surface of the substrate at regular intervals along a longitudinal direction and a lateral direction of the first surface,
    wherein the substrate has a plurality of first grooves formed between the plurality of fine needles on the first surface and a plurality of second grooves formed on the second surface such that the plurality of second grooves is positioned to correspond to positions of the plurality of fine needles and offset from the plurality of first grooves and has a depth that does not fluidly connect to the plurality of first grooves in a thickness direction of the substrate, such that the substrate deforms to follow a surface shape of a skin and such that the plurality of first grooves and the plurality of second grooves allow axes of the plurality of fine needles to extend in a direction normal to the surface of the skin, the plurality of first grooves includes a set of grooves extending in a first direction between adjacent ones of the plurality of fine needles, and arrayed along a second direction perpendicular to the first direction, and the plurality of second grooves includes a set of grooves extending in a third direction, and arrayed along a fourth direction perpendicular to the third direction.

2. The needle assembly of claim 1, wherein each of the plurality of first grooves and the plurality of second grooves has at least one cross section selected from trapezoidal, rectangular, triangular, semicircular, and semielliptical in a direction perpendicular to a direction in which each of the plurality of first grooves and the plurality of second grooves extend.

3. The needle assembly of claim 1, wherein the plurality of first grooves includes a second set of grooves extending in the second direction perpendicular to the first direction.

4. The needle assembly of claim 3, wherein the plurality of second grooves includes a second set of grooves extending in the fourth direction perpendicular to the third direction.

5. The needle assembly of claim 4, wherein the plurality of first grooves is formed such that the first direction is the longitudinal direction of the first surface, and the plurality of second grooves is formed such that the third direction is a longitudinal direction of the second surface.

6. The needle assembly of claim 4, wherein the plurality of first grooves is formed such that the first direction is the longitudinal direction of the first surface, and the plurality of second grooves is formed such that the third direction is a diagonal direction of the second surface.

7. The needle assembly of claim 1, wherein the plurality of first grooves is formed such that the first direction is the longitudinal direction of the first surface.

8. The needle assembly of claim 1, wherein the plurality of first grooves is formed such that the first direction is the lateral direction of the first surface.

9. The needle assembly of claim 1, wherein the plurality of first grooves is formed such that the first direction is a diagonal direction of the first surface.

10. The needle assembly of claim 1, wherein the plurality of second grooves is formed such that the plurality of second grooves is positioned to substantially correspond to the axes of the plurality of fine needles on the first surface of the substrate.

11. The needle assembly of claim 10, wherein the plurality of first grooves includes a second set of grooves extending in the second direction perpendicular to the first direction, and the plurality of second grooves includes a second set of grooves extending in the fourth direction perpendicular to the third direction.

12. The needle assembly of claim 10, wherein the plurality of first grooves is formed such that the first direction is the longitudinal direction of the first surface.

13. The needle assembly of claim 10, wherein the plurality of first grooves is formed such that the first direction is the lateral direction of the first surface.

14. The needle assembly of claim 10, wherein the plurality of first grooves is formed such that the first direction is a diagonal direction of the first surface.

15. The needle assembly of claim 1, wherein the plurality of first grooves is formed such that each of the plurality of first grooves has a length that is less than a length of the first surface of the substrate in a direction in which each of the plurality of first grooves extends.

16. The needle assembly of claim 1, wherein the plurality of first grooves is formed such that adjacent first grooves are spaced apart from each other by two adjacent fine needles.

17. The needle assembly of claim 1, wherein the plurality of first grooves is formed such that adjacent first grooves are spaced apart from each other by three adjacent fine needles.

18. The needle assembly of claim 1, wherein the plurality of second grooves is formed such that the first direction is the longitudinal direction of the first surface, and the third direction is one of a longitudinal direction and a lateral direction of the second surface.

19. A method of producing a needle assembly for transdermal administration, comprising:
    placing a polymer material on a surface of a reproduction plate having a flat part, a plurality of recesses corresponding to a plurality of fine needles, and a plurality of projections corresponding to a plurality of first grooves;
    heating the polymer material such that the polymer material melts on the reproduction plate;
    pressing the polymer material with a press having a flat surface portion facing the flat part of the reproduction plate and a plurality of projecting portions formed offset from the plurality of projections of the reproduction plate such that the plurality of projecting portions corresponds to a plurality of second grooves;
    curing the polymer material on the reproduction plate such that a needle assembly is formed; and
    releasing the needle assembly from the reproduction plate to obtain the needle assembly comprising a substrate having a first surface and a second surface opposite to the first surface, and the plurality of fine needles projecting perpendicularly from the first surface and positioned in a matrix on the first surface of the substrate at regular intervals along a longitudinal direction and a lateral direction of the first surface, wherein the substrate has the plurality of first grooves formed between the plurality of fine needles on the first surface and the plurality of second grooves formed on the second surface such that the plurality of second grooves is positioned to correspond to positions of the plurality of fine needles and offset from the plurality of first grooves and has a depth that does not fluidly connect to the plurality of first grooves in a thickness direction of the substrate, such that the substrate deforms to follow a surface shape of a skin and such that the plurality of first grooves and the plurality of second grooves allow axes of the plurality of fine needles to extend in a direction normal to the surface of the skin, the plurality of first grooves includes a set of grooves extending in a first direction between adjacent ones of the plurality of fine needles, and arrayed along a second direction perpendicular to the first direction, and the plurality of second grooves includes a set of grooves extending in a third direction, and arrayed along a fourth direction perpendicular to the third direction.

20. The method of claim 19, wherein the polymer material is a biocompatible thermoplastic resin.

* * * * *